(12) United States Patent
Buzawa

(10) Patent No.: US 7,909,816 B2
(45) Date of Patent: Mar. 22, 2011

(54) DIRECTIONAL PROBE TREATMENT APPARATUS

(75) Inventor: David M. Buzawa, San Jose, CA (US)

(73) Assignee: Iridex Corporation, Mountain View, CA (US)

( * ) Notice: Subject to any disclaimer, the term of this patent is extended or adjusted under 35 U.S.C. 154(b) by 1017 days.

(21) Appl. No.: 11/205,629

(22) Filed: Aug. 16, 2005

(65) Prior Publication Data

US 2006/0041291 A1    Feb. 23, 2006

Related U.S. Application Data

(60) Provisional application No. 60/602,166, filed on Aug. 16, 2004.

(51) Int. Cl.
*A61F 9/007* (2006.01)
*A61F 9/008* (2006.01)
*A61F 9/011* (2006.01)

(52) U.S. Cl. ............... 606/4; 606/5; 606/13; 606/15; 606/41; 607/89; 607/101

(58) Field of Classification Search ............ 607/10, 607/89, 101; 606/4, 5, 7, 13, 15, 17, 41, 606/113
See application file for complete search history.

(56) References Cited

U.S. PATENT DOCUMENTS

| | | | |
|---|---|---|---|
| 4,537,193 A | | 8/1985 | Tanner |
| 4,593,691 A | * | 6/1986 | Lindstrom et al. ............ 606/45 |
| 4,822,360 A | * | 4/1989 | Deacon ...................... 623/6.13 |
| 4,863,430 A | * | 9/1989 | Klyce et al. ............. 604/170.03 |
| 5,755,714 A | * | 5/1998 | Murphy-Chutorian ........ 606/15 |
| 6,142,990 A | * | 11/2000 | Burk ................................ 606/6 |
| 6,752,608 B1 | * | 6/2004 | Yap .................................. 418/63 |
| 6,984,230 B2 | * | 1/2006 | Scheller et al. ................. 606/15 |
| 2002/0087047 A1 | * | 7/2002 | Remijan et al. .............. 600/109 |
| 2003/0191461 A1 | * | 10/2003 | Scheller et al. ................ 606/15 |

OTHER PUBLICATIONS

IRIDEX Press Release, "IRIDEX Expands EndoPorbe product Family With Unique Stepping Probes" (Apr. 16, 2005) IRIDEX Corporation, 1212 Terra Bella Avenue, Mountain View, CA , 94043-1824, 2 pages total.

* cited by examiner

*Primary Examiner* — Roy D Gibson
*Assistant Examiner* — Kaitlyn E Helling
(74) *Attorney, Agent, or Firm* — Kilpatrick Townsend & Stockton

(57) ABSTRACT

A treatment apparatus includes a cannula with a cannula lumen. The cannula has a first average diameter. A probe is positionable in the cannula lumen. The probe has a first section with a second average diameter and a second section with a third average diameter that is less than the second average diameter. At least a portion of the second section has a curved section with at least one radius of curvature. The radius of curvative is selected to provide that as the second section passes through the cannula lumen a first side of the second section is tangential to a first side of the cannula lumen, and a second opposing side of the second section is tangential to a second opposing side of the cannula lumen.

27 Claims, 4 Drawing Sheets

Sample calculations determining cannula compatibility with instruments of various radius of curvature and outside diameter Table plots minimum bend radius R that still permits passage of a curved instrument such as a needle or probe through a cannula without interference. Clearance "s", length of cannula "z" and resultant minimum bend radius "R" are related by the formula: $= R - (R^2 - r^2)^{0.5}$, or $R = (s^2 + r^2)/2s$. All bend radii greater than "R" will also pass through the cannula without interference. All dimensions in inches.

Example 1: 20 gauge x 4mm long cannula

| Diameter of angled portion of instrument "D1" | | "D2" | "s" | "z" | "R" | Arc length for bends of various degrees | | | Chord length for bends of various degrees | | |
|---|---|---|---|---|---|---|---|---|---|---|---|
| Gauge | Maximum OD (inches) | Cannula ID min | Clearance min | Cannula Length | Minimum Bend Radius | 15 | 30 | 45 | 15 | 30 | 45 |
| 20 | 0.0360 | 0.0400 | 0.0040 | 0.1600 | 0.8020 | 0.210 | 0.420 | 0.630 | 0.209 | 0.415 | 0.614 |
| 21 | 0.0325 | 0.0400 | 0.0075 | 0.1600 | 0.4304 | 0.113 | 0.225 | 0.338 | 0.112 | 0.223 | 0.329 |
| 22 | 0.0285 | 0.0400 | 0.0115 | 0.1600 | 0.2840 | 0.074 | 0.149 | 0.223 | 0.074 | 0.147 | 0.217 |
| 23 | 0.0255 | 0.0400 | 0.0145 | 0.1600 | 0.2279 | 0.060 | 0.119 | 0.179 | 0.060 | 0.118 | 0.174 |
| 24 | 0.0225 | 0.0400 | 0.0175 | 0.1600 | 0.1916 | 0.050 | 0.100 | 0.150 | 0.050 | 0.099 | 0.147 |
| 25 | 0.0205 | 0.0400 | 0.0195 | 0.1600 | 0.1739 | 0.046 | 0.091 | 0.137 | 0.045 | 0.090 | 0.133 |
| 26 | 0.0185 | 0.0400 | 0.0215 | 0.1600 | 0.1596 | 0.042 | 0.084 | 0.125 | 0.042 | 0.083 | 0.122 |
| 27 | 0.0165 | 0.0400 | 0.0235 | 0.1600 | 0.1479 | 0.039 | 0.077 | 0.116 | 0.039 | 0.077 | 0.113 |
| 28 | 0.0145 | 0.0400 | 0.0255 | 0.1600 | 0.1382 | 0.036 | 0.072 | 0.109 | 0.036 | 0.072 | 0.106 |

Example 2: 25 gauge x 5mm long cannula

| Diameter of angled portion of instrument "D1" | | "D2" | "s" | "z" | "R" | Arc length for bends of various degrees | | | Chord length for bends of various degrees | | |
|---|---|---|---|---|---|---|---|---|---|---|---|
| Gauge | Maximum OD (inches) | Cannula ID min | Clearance min | Cannula Length | Minimum Bend Radius | 15 | 30 | 45 | 15 | 30 | 45 |
| 25 | 0.0205 | 0.0210 | 0.0005 | 0.2000 | 10.0003 | 2.618 | 5.236 | 7.854 | 2.611 | 5.177 | 7.654 |
| 26 | 0.0185 | 0.0210 | 0.0025 | 0.2000 | 2.0013 | 0.524 | 1.048 | 1.572 | 0.522 | 1.036 | 1.532 |
| 27 | 0.0165 | 0.0210 | 0.0045 | 0.2000 | 1.1134 | 0.291 | 0.583 | 0.874 | 0.291 | 0.576 | 0.852 |
| 28 | 0.0145 | 0.0210 | 0.0065 | 0.2000 | 0.7725 | 0.202 | 0.404 | 0.607 | 0.202 | 0.400 | 0.591 |
| 29 | 0.0135 | 0.0210 | 0.0075 | 0.2000 | 0.6704 | 0.176 | 0.351 | 0.527 | 0.175 | 0.347 | 0.513 |
| 30 | 0.0125 | 0.0210 | 0.0085 | 0.2000 | 0.5925 | 0.155 | 0.310 | 0.465 | 0.155 | 0.307 | 0.453 |

*FIG. 2*

DIRECTIONAL PROBE TREATMENT APPARATUS

This application claims the benefit of priority to U.S. Provisional Application Ser. No. 60/602,166 filed Aug. 16, 2004 and is fully incorporated herein by reference for all purposes.

BACKGROUND OF THE INVENTION

Ophthalmic surgeons using straight cannula to help introduce instruments into the globe have been limited to date to the use of straight, rigid instruments, or too deformable ("directional") instruments. Such instruments must first pass through the cannula in an essentially straight configuration. The instrument is then deflected into some angle that is controlled by the surgeon.

The small dimensions associated with devices used in ophthalmic and other microsurgeries can result in higher rates of mechanical failure of instruments during use.

There is a need for a directional probe that has the durability and consistent geometry of a rigid instrument. There is a further need for a directional probe that does not have moving parts which helps to ensure structural integrity of the inserted portion of the instrument. There is yet another need for a directional probe that has a monolithic geometry which is stronger than hardware employing flexible or deformable features and simultaneously provides angulation and cannula compatibility.

SUMMARY OF THE INVENTION

The present invention provides solutions for at least some of the issues discussed above. Specifically, some embodiments of the present invention provide an improved apparatus that has the consistent geometry and durability of a rigid instrument. The present invention also provided techniques for manufacturing and sizing the probes and cannulas to be usable with one another. At least some of these and other objectives described herein will be met by embodiments of the present invention.

In one embodiment of the present invention, a directional probe is provided that has the durability and consistent geometry of a rigid instrument. The directional probe may be designed so that it does not have moving parts which helps to ensure structural integrity of the inserted portion of the instrument. In yet another embodiment, a directional probe may have a monolithic geometry which is stronger than hardware employing flexible or deformable features and simultaneously provides angulation and cannula compatibility.

In yet another embodiment of the present invention, a treatment apparatus includes a cannula with a cannula lumen. The cannula has a first average diameter. A probe is positionable in the cannula lumen. The probe has a first section with a second average diameter and a second section with a third average diameter that is less than the second average diameter. At least a portion of the second section has a curved section with at least one radius of curvature. The radius of curvative is selected to provide that as the second section passes through the cannula lumen a first side of the second section is tangential to a first side of the cannula lumen, and a second opposing side of the second section is tangential to a second opposing side of the cannula lumen.

Any of the above embodiments may have features as listed below. For example, the apparatus may have a seal that is created between the cannula and the probe when the probe is positioned in the cannula. The seal may be characterized by the simple close fit of noncompliant materials and surfaces. A major portion of the cannula may have a substantially linear geometry. The cannula may have a tissue penetrating distal end. The probe may have a tissue penetrating distal end. The probe may be rotationally moveable within the cannula when positioned in the cannula. The probe may be moveable in a direction along a longitudinal axis of the cannula when positioned in the cannula. The distal portion of the probe may be configured to provide access to a swept region within a tissue site. In one embodiment, the first diameter may be about 20 gauge to 25 gauge. In another embodiment, the second diameter may be about 20-30 gauge. In yet another embodiment, at least first radius of curvature is 3-30 mm. The probe may have a probe lumen. The probe lumen may be sufficiently sized to receive an optical fiber. The probe lumen may be sufficiently sized to receive an RF electrode. The probe lumen may be sufficiently sized to receive a resistive heating device. The probe lumen may be sufficiently sized to receive an ultrasound device. In one embodiment, the probe is an angled probe with a single outside dimension that is smaller of a diameter of the cannula and a separately provided sleeve that can slip over the outside dimension of the probe and provide a seal with the inside diameter of the cannula. In one embodiment, a clearance S exists between cannula and probe, a length of cannula is 2r, and resultant minimum bend radius of the probe is R, and wherein the bend radius R is based on the following formula: $R=(s^2+r^2)/2s$ In another embodiment of the present invention, a method of treatment is provided that includes providing a treatment device a cannula with a cannula lumen, a probe positionable in the cannula lumen, the probe having a first section with a second average diameter and a second section with a third average diameter that is less than the second average diameter, at least a portion of the second section having a curved section with at least one radius of curvature. The method may include introducing a distal section of the cannula into a tissue; introducing the probe through the cannula lumen with a first side of the second section being tangential to a first side of the cannula lumen, and a second opposing side of the second section being tangential to a second opposing side of the cannula lumen; and advancing a distal portion of the probe into a tissue site of the tissue.

With any of the methods herein, the method may further include any of the features or steps disclosed below. For example, the method may include introducing a treatment device through a probe lumen. The treatment device may include an optical fiber, an RF electrode, a resistive heating delivery member, and/or an ultrasound delivery member. The method may include rotating the probe when it is positioned in the cannula lumen. The probe may move in a longitudinal direction relative to an axis of the cannula's lumen. The tissue site may be in an interior of an eye. In one embodiment, the probe may be an angled probe with a single outside dimension that is smaller of a diameter of the cannula and a separately provided sleeve that can slip over the outside dimension of the probe and provide a seal with the inside diameter of the cannula. For any of the above, the probe and cannula may be sized and shaped substantially consistent to that described in FIG. 2.

A further understanding of the nature and advantages of the invention will become apparent by reference to the remaining portions of the specification and drawings.

BRIEF DESCRIPTION OF THE DRAWINGS

FIG. 2 is a table summary sample calculations determining the compatibility of a cannula with probes with different diameters from the FIG. 1(*a*) embodiment.

DETAILED DESCRIPTION OF THE PREFERRED EMBODIMENTS

Figure 1A:
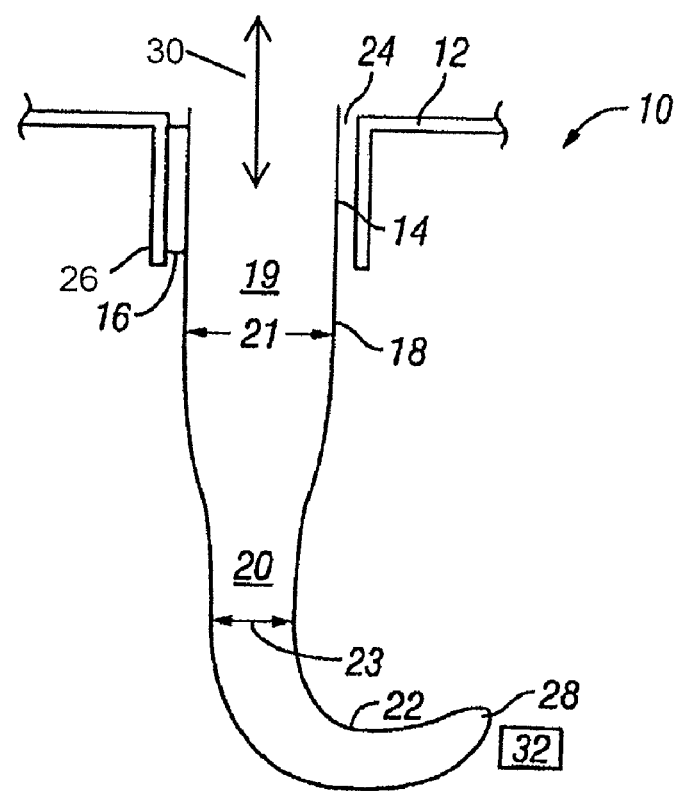
FIG. 1(a) is a cross-sectional view of one embodiment of a directional probe of the present invention.
Figure 1B:
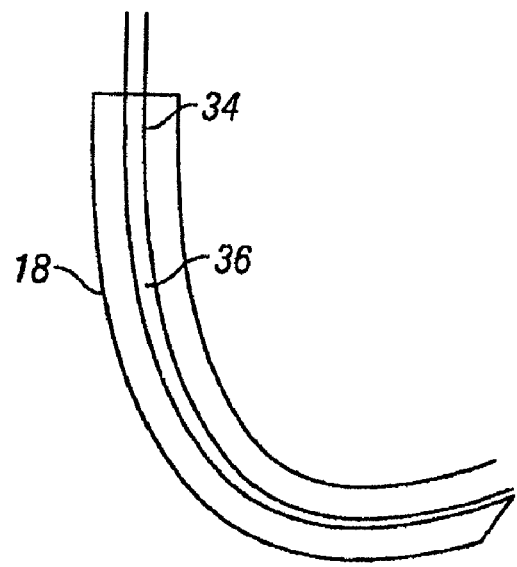
FIG. 1(*b*) is a cross-sectional view of a probe that is used with the FIG. 1(*a*) embodiment.

Referring to FIG. 1, one embodiment of the present invention is a directional probe, generally denoted as 10, that has a cannula 12 with a cannula lumen 14. Cannula lumen 14 has an average diameter 16. In one embodiment, average diameter 16 is about from 20-25 gauge. 20 and 25 gauge are both important in ophthalmic surgery. Dimensions much smaller than 25 gauge, higher gauge number, such as 26 gauge, 27, gauge are less important due to incompatibility with existing support instrumentation and the increasing difficulty coupling therapeutic modalities such as laser, electrosurgery, diathermy, and the like.

A probe 18 is positionable in cannula lumen 14. Probe 18 has a first section 19 with a first average diameter 21, a distal portion 20 with a curved section 22 that has at least one radius of curvature and with a second average diameter 23. In one embodiment second average diameter is the range of about 20-30 gauge. Second average diameter 23 is less than first average diameter.

In one embodiment, directional probe 18 is a rigid instrument that offers the treatment access of an angled device and is simultaneously compatible with an instrument introducing cannula. In one embodiment, directional probe 18 is useful for use by ophthalmic surgeons to help introduce instruments into the globe. Directional probe 10 provides convenience and capability of a standard directional probe in combination with the durability and consistent geometry of a rigid instrument.

Generally, directional probe 10 has few if any moving parts. This ensures structural integrity of the inserted portion of the directional probe 10. Directional probe 10 can have small dimensions and is particularly useful in ophthalmic and other microsurgeries. Directional probe 10 can have a monolithic geometry that is stronger than hardware employing flexible or deformable features to simultaneously achieve angulation and cannula compatibility.

Curved section 22 can have numerous radii of curvature. The curvature of curved section 22 is selected to ensure passage of curved section 22 through the length of cannula 12 without interference. In one embodiment, the curvature of curved section 22 is 3-30 mm. As a nonlimiting example, radii less than 3 mm are only compatible with extremely short cannula which are used often. Such short radii are also not compatible with the minimum bend radius requirements of most multimode optical fibers. As another nonlimiting example, radii greater than 30 mm are sometimes larger than the human eye, precluding their use in invasive ophthalmic surgery. In one embodiment, the curvature of curved section 22 that is selected to provide that as distal portion 20 passes through cannula lumen 14, a first side of distal portion 20 is tangential to a first side of cannula lumen 14, and a second opposing side of the distal portion 20 is tangential to a second opposing side of cannula lumen 14.

In one embodiment, a seal 24 is created between cannula 12 and probe 18 when the probe is positioned in cannula 12. Seal 24 provides a simple close fit of noncompliant materials and surfaces of cannula 12 and probe 18. In one embodiment, a major portion of cannula 12 has a substantially linear geometry.

Cannula 12 may have a tissue penetrating distal end 26. Probe 18 may also have a tissue penetrating distal end 28.

Probe 18 is rotationally moveable within cannula 12 when positioned in the cannula lumen 14. Probe 18 is also moveable in a direction, generally denoted as 30, along a longitudinal axis of cannula 12 when positioned in cannula lumen 14. A distal portion of probe 18 is configured to provide access to a swept region, denoted as 32, within a tissue site.

Referring now to FIG. 1(*b*), probe 18 has a probe lumen 34. Probe lumen 34 is sized to receive a treatment device 36. By way of example and not limitation, treatment device 36 can be, an optical fiber, an RF electrode, a resistive heating device, an ultrasound device, and the like.

FIG. 2 is a table summary sample calculations determining the compatibility of cannula 12 with probes 18 with different diameters. By way of example and not limitation, FIG. 2 shows that a formula may be used to determine a clearance S, a length of cannula 2r and resultant minimum bend radius R. In one embodiment, the formula may be $s = R - (R^2 - r^2)^{0.5}$ or $R = (s^2 + r^2)/2s$. Table 2 also shows Arc length for bends of various degrees and chord lengths for bends of various degrees. These same sizes may be used for embodiments such as those described in FIG. 4 for the probe 50. In some embodiment, the cannula 12 may have the length of 2r or less.

Figure 3:
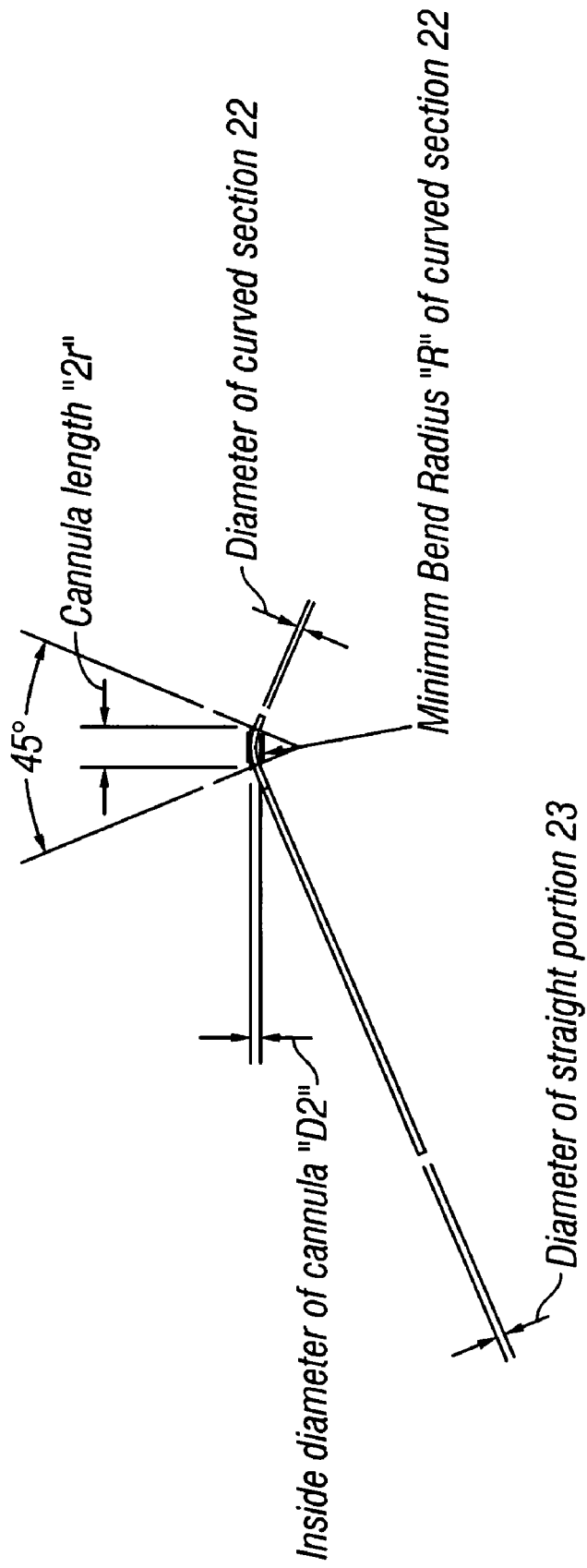
FIG. 3 illustrates the relationship of the different diameters of the probe and cannula of the FIG. 1(*a*) embodiment.

FIG. 3 relates the various diameters. In one embodiment of the present invention, directional probe 10 is used for a variety of different methods of treatment. Cannula 12 is introduced into a tissue. Probe 18 is introduced through cannula lumen 14. A first side of the curved section 22 is tangential to a first side of cannula lumen 14, and a second opposing side of curved section 22 is tangential to a second opposing side of cannula lumen 14. Distal portion 20 of probe 18 is advanced into a tissue site of the tissue. A treatment device is introduced through a lumen of probe 18. Treatment device can be a variety of different devices, including but not limited to, an optical fiber, an RF electrode. a resistive heating delivery member, an ultrasound delivery member, and the like. Probe 18 can then be rotated and/or moved in a longitudinal direction relative to an axis of the cannula lumen 14. The tissue site can be a variety of different tissue sites including but not limited to the eye.

Figure 4:
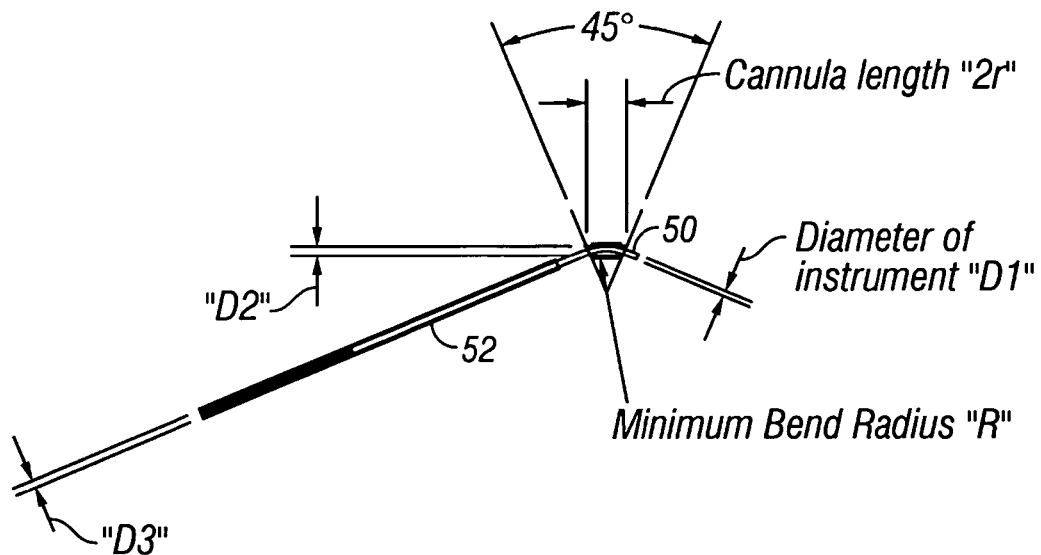
FIG. 4 shows another embodiment of the present invention.

Referring now to FIG. 4, another embodiment of the present invention may be divided into two separate pieces, and provide an angled probe 50 with a single outside dimension D1 that is the smaller of the diameters (30 gauge for example) and separately provide a flexible plastic or slit metal sleeve 52 that can slip over the outside diameter D1 and provide a seal with the inside diameter D2 of the cannula (25 gauge for example, not shown for ease of illustration). The sleeve 52 has a diameter D3. In one embodiment, this allows a probe 50 of a constant diameter D1 to be adapted for use with a larger cannula through the use of a sleeve 52. By way of example and not limitation, the probe 50 may have a bend radius R sized for use with a cannula (not shown) based on the chart in FIG. 2. In one embodiment, the sleeve 52 has a constant diameter D3. In other embodiments, the sleeve 52 may have a tapered configuration or other configuration with varying diameters.

Figure 5:
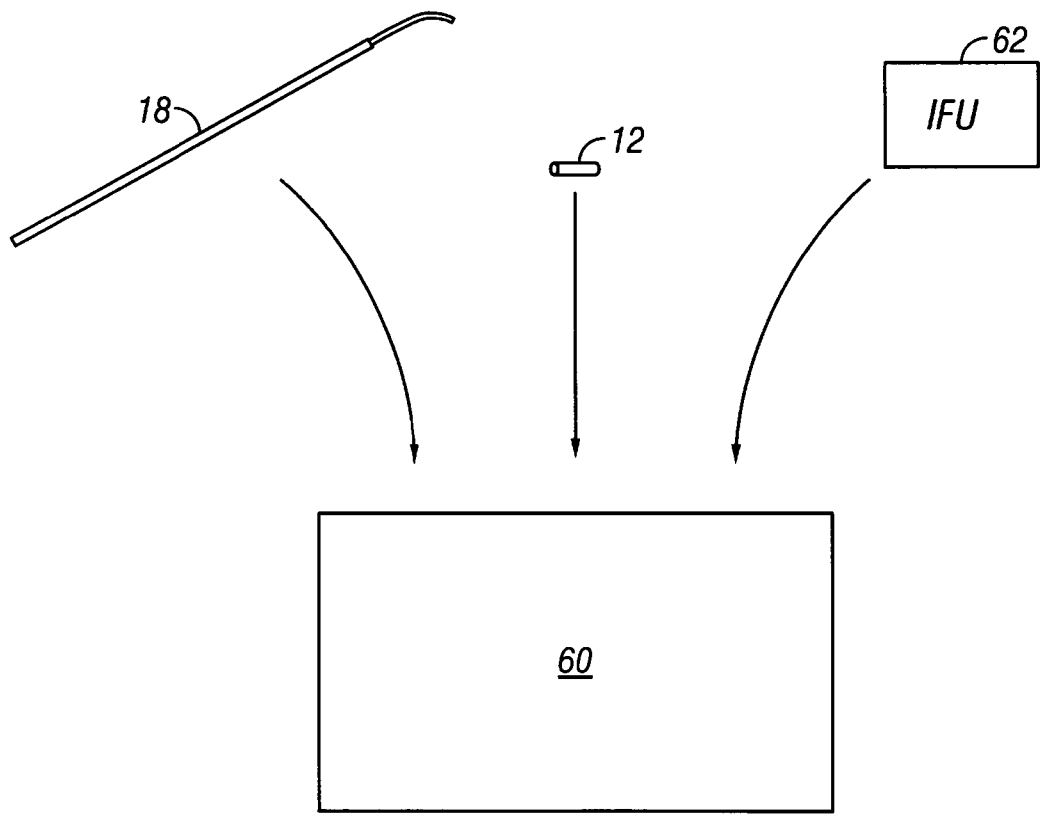
FIG. 5 shows a kit according to the present invention.

FIG. 5 shows one embodiment of a kit according to the present invention. The kit may include a container 60 such but not limited to bag, pouch, box, hermetically sealed container, or the like that will receive a probe 18 and at least the instructions for use (IFU) 62. Optionally, an appropriately sized cannula 12 such as described or sized per FIG. 2 may be included in the container 60. Other embodiments may substitute probe 18 with probe 50 and sleeve 52. The IFU may set forth a variety of methods including: providing a treatment device a cannula with a cannula lumen, a probe positionable in the cannula lumen, the probe having a first section with a second average diameter and a second section with a third average diameter that is less than the second average diameter, at least a portion of the second section having a curved section with at least one radius of curvature; introducing a distal section of the cannula into a tissue; introducing the probe through the cannula lumen with a first side of the second section being tangential to a first side of the cannula lumen, and a second opposing side of the second section being tangential to a second opposing side of the cannula lumen; and advancing a distal portion of the probe into a tissue site of the tissue.

The foregoing description of a preferred embodiment of the invention has been presented for purposes of illustration and description. It is not intended to be exhaustive or to limit the invention to the precise forms disclosed. Additionally, U.S. Provisional Application Ser. No. 60/602,166 is fully incorporated herein by reference for all purposes. Obviously, many modifications and variations will be apparent to practitioners skilled in this art. It is intended that the scope of the invention be defined by the following claims and their equivalents.

What is claimed is:

1. An apparatus for treating an eye, comprising:
   a rigid cannula with a cannula lumen and having an inside diameter between about 20-25 gauge; and
   a rigid probe with an outside diameter that is smaller than the inside diameter of the cannula, the probe rotationally and axially positionable in the cannula lumen, and having a distal portion with a curved section that has at least one radius of curvature, the at least one radius of curvature selected to ensure passage of the curved section of the probe through the length of the cannula without interference;
   wherein the distal portion of the probe in use provides access to a region within an interior of the eye so as to allow the distal portion of the probe to sweep the region along the interior of the eye without flexing or deforming the probe.

2. The apparatus of claim 1, wherein a seal is created between the inside diameter of the cannula and the outside diameter of the probe when the probe is positioned in the cannula.

3. The apparatus of claim 2, wherein the seal is characterized by the simple close fit of noncompliant materials and surfaces.

4. The apparatus of claim 1, wherein a major portion of the cannula has a substantially linear geometry.

5. The apparatus of claim 1, wherein the cannula has a tissue penetrating distal end.

6. The apparatus of claim 5, wherein the probe has a tissue penetrating distal end.

7. The apparatus of claim 1, wherein the probe is rotationally moveable within the cannula when positioned in the cannula.

8. The apparatus of claim 1, wherein the probe is moveable in a direction along a longitudinal axis of the cannula when positioned in the cannula.

9. The apparatus of claim 1, wherein the at least one radius of curvature is 3-30 mm.

10. The apparatus of claim 1, wherein the probe has a probe lumen.

11. The apparatus of claim 1, wherein the probe has a lumen, and wherein the probe lumen is sufficiently sized to receive an optical fiber.

12. The apparatus of claim 1, wherein the probe has a lumen, and wherein the probe lumen is sufficiently sized to receive an RF electrode.

13. The apparatus of claim 1, wherein the probe has a lumen, and wherein the probe lumen is sufficiently sized to receive a resistive heating device.

14. The apparatus of claim 1, wherein the probe has a lumen, and wherein the probe lumen is sufficiently sized to receive an ultrasound device.

15. The apparatus of claim 1, wherein the probe has a substantially constant diameter and further comprising a sleeve slidable over the probe, said sleeve having an inner diameter sized to engage the probe and an outer diameter sized to engage an inner diameter of the cannula.

16. The device of claim 1, wherein a clearance s exists between cannula and probe, a length of cannula is 2r, and resultant minimum bend radius of the probe is R, and wherein the minimum bend radius R is based on the following relationship: $R=(s^2+r^2)/2s$.

17. An treatment apparatus for treating an eye, comprising:
    a cannula with a rigid cannula lumen with a first average diameter between about 20-25 gauge;
    a probe positionable in the cannula lumen, the probe having a first rigid section with a second average diameter and a second rigid section with a third average diameter that is less than the second average diameter, at least a portion of the second section having a curved section with at least one rigid radius of curvature, the at least one radius of curvature selected to provide that as the second section passes through the cannula lumen a first side of the second section is tangential to a first side of the cannula lumen, and a second opposing side of the second section is tangential to a second opposing side of the cannula lumen;
    wherein the second section of the probe in use provides access to a region within an interior of the eye so as to allow the second section of the probe to sweep the region along the interior of the eye without flexing or deforming the probe.

18. A method of treating an eye, comprising:
    providing an apparatus including a rigid cannula with a cannula lumen, and also including a rigid probe positionable in the cannula lumen, the probe having a first rigid section with a second average diameter and a second rigid section with a third average diameter that is less than the second average diameter, at least a portion of the second section having a curved section with at least one radius of curvature;
    introducing a distal section of the cannula into the eye;
    introducing the probe through the cannula lumen with a first side of the second section being tangential to a first side of the cannula lumen, and a second opposing side of the second section being tangential to a second opposing side of the cannula lumen; and
    advancing a distal portion of the probe into a tissue site inside the eye; and
    sweeping a region within an interior of the eye without flexing or deforming the probe.

19. The method of claim 18, further comprising:
    introducing a treatment device through a lumen of the probe.

20. The method of claim 19, wherein the treatment device includes an optical fiber.

21. The method of claim 19, wherein the treatment device includes an RF electrode.

22. The method of claim 19, wherein the treatment device includes a resistive heating delivery member.

23. The method of claim 19, wherein the treatment device includes an ultrasound delivery member.

24. The method of claim 18, further comprising:
rotating the probe when it is positioned in the cannula lumen.

25. The method of claim 18, further comprising:
moving the probe in a longitudinal direction relative to an axis of the cannula's lumen.

26. The method of claim 18, wherein a clearance s exists between cannula and probe, a length of cannula is 2r, and resultant minimum bend radius of the probe is R, and wherein the minimum bend radius R is based on the following relationship: $R=(s^2+r^2)/2s$.

27. The method of claim 18, further comprising a sleeve between the cannula and probe.

* * * * *